United States Patent
Hargens et al.

(10) Patent No.: US 8,008,378 B2
(45) Date of Patent: Aug. 30, 2011

(54) TASTE-MASKED COMPOSITION OF CATIONIC EXCHANGE RESIN

(75) Inventors: Robert D. Hargens, Lincoln, NE (US); Yimin Jia, Lincoln, NE (US); Greg Slominski, Elmwood, NE (US); Suresh Vayalakkada, Lincoln, NE (US)

(73) Assignee: Novartis AG (CH)

( * ) Notice: Subject to any disclaimer, the term of this patent is extended or adjusted under 35 U.S.C. 154(b) by 961 days.

(21) Appl. No.: 10/566,188

(22) PCT Filed: Jul. 27, 2004

(86) PCT No.: PCT/EP2004/008394
§ 371 (c)(1),
(2), (4) Date: Jun. 15, 2007

(87) PCT Pub. No.: WO2005/013934
PCT Pub. Date: Feb. 17, 2005

(65) Prior Publication Data
US 2008/0044371 A1 Feb. 21, 2008

(51) Int. Cl.
| | |
|---|---|
| *C08G 18/67* | (2006.01) |
| *C08L 23/26* | (2006.01) |
| *A61J 3/00* | (2006.01) |
| *A61J 3/06* | (2006.01) |
| *C08J 7/00* | (2006.01) |
| *C08J 7/02* | (2006.01) |
| *C08J 7/04* | (2006.01) |
| *C08J 3/00* | (2006.01) |
| *C08J 3/03* | (2006.01) |

(52) U.S. Cl. ............ 524/86; 524/37; 524/500; 524/501; 524/580; 524/745; 524/848; 524/700; 524/742; 424/439; 424/464; 424/474; 424/483; 514/974

(58) Field of Classification Search .............. 524/86, 524/37, 500, 501, 580, 700, 742, 745, 848; 424/78.1, 439, 464, 474, 483; 514/974
See application file for complete search history.

(56) References Cited

U.S. PATENT DOCUMENTS
7,067,116 B1 * 6/2006 Bess et al. .................. 424/78.1

FOREIGN PATENT DOCUMENTS
| EP | 0 367 746 | 5/1990 |
|---|---|---|
| EP | 0 943 341 | 9/1999 |
| EP | 1 175 915 | 1/2002 |
| EP | 1175915 | * 1/2002 |
| WO | WO 92/01443 | 2/1992 |
| WO | WO 01/70194 | 9/2001 |
| WO | WO 03/061709 | 7/2003 |

OTHER PUBLICATIONS

Squillante et al "Extended Release Chlorpheniramine Maleate from Polymethacrylate Solid Dispersions by Supercritical Fluid Processing", Drug Delivery Technolgy, vol. 2, No. 5, pp. 58-64, (2002).
Rudraraju et al., "Ion Exchange Resinates Containing Chlorpheniramine Maleate", Pharmaceutical Research, vol. 9, p. 5163 (1992).
Nanda et al, "An Update on Taste Masking Technologies for Oral Pharmaceuticals", Indian Journal of Pharmaceutical Sceinces, vol. 64, No. 1, pp. 10-17, (2002).
Agarwal et al, "Studies of Ion Exchange Resin Complex of Chloroquine Phosphate", Drug Development and Industrial Pharmacy, vol. 26, No. 7, pp. 773-776, (2000).
John Beyers, "Solvent Poloarity and Miscribility", Internet Article, Online XP002317825.

\* cited by examiner

*Primary Examiner* — James J Seidleck
*Assistant Examiner* — Deve E Valdez
(74) *Attorney, Agent, or Firm* — Frank A. Smith

(57) ABSTRACT

The present invention provides a taste-masked composition containing an active compound. The composition is taste-masked by employing a loaded polymeric matrix which is produced by incorporating or complexing the active compound on a polymeric matrix having ionic functional groups and removing unbound active compounds from the polymeric matrix.

8 Claims, No Drawings

TASTE-MASKED COMPOSITION OF CATIONIC EXCHANGE RESIN

The present invention relates to a taste-masking technology particularly suitable for active administering preparations.

There are many different approaches to taste-mask pharmaceutically or physiologically active compounds that have a disagreeable taste profile. One approach uses a high intensity sweetener or flavor to overpower the disagreeable taste of the active compound. Another approach uses an adsorbent material to adsorb the active compound such that the active compound becomes available mostly after the active-containing adsorbate passes the oral cavity. Adsorbent materials used in this approach include silicon dioxide, copolymers of acrylates, silicate, and ion exchange resins.

The approach of utilizing an ion exchange resin to taste-mask a pharmaceutical formulation for oral administration has been explored for some time. However, the concentration of an active compound that can be loaded in the adsorbate and the effectiveness of taste-masking of the loaded adsorbate continue to be unsatisfactory.

SUMMARY OF THE INVENTION

The present invention provides a taste-masked composition containing a physiologically or pharmaceutically active compound. The composition is taste-masked by preparing a loaded polymeric matrix which is produced by incorporating or complexing the active compound on a polymeric matrix having ionic functional groups. After the matrix is loaded with the active compound, it is washed with a nonpolar solvent such that the washing step does not cause dissociation of bound active molecules from the loaded matrix. According to the present invention, a taste-masked composition is produced by loading an active compound on a polymeric matrix having ionic functional groups and washing the loaded matrix to remove unbound active compounds without causing competing dissociation of the bound active from the matrix. As one embodiment, the taste-masked composition has a cation exchange resin which contains anionic functional groups and a basic active compound bound thereto, wherein at least 60% of the functional groups of the cation exchange resin are bound by the active compound, and the ion exchange resin composition is substantially free of the active compound that is not bound to the cation exchange resin. The term substantially free as used herein indicates the level of concentration that is lower than the amount that can be detected by the human taste sensory organ. Additionally provided is a process for improving organoleptic properties of a hydrogen form cation ion exchange resin. The process has the step of neutralizing the ion exchange resin with a metal ion. Further provided as a specific embodiment is a taste masked composition containing an ion exchange resin having carboxylic acid functional groups and dextromethrophan, wherein the composition is substantially free of unbound dextromethrophan and is adapted for rapidly releasing dextromethorphan in the stomach.

Thus, the invention concerns, inter alia, a process for producing a taste-masked composition comprising a basic active compound and a polymeric matrix having anionic functional groups, said process comprising the steps of loading said polymeric matrix with said active compound to produce a loaded matrix, and washing said loaded matrix with a nonpolar solvent.

The invention further concerns, inter alia, a pharmaceutically active resin composition comprising a cation exchange resin having an anionic functional group and a basic active compound which is loaded to said cation exchange resin, wherein at least about 50 wt % of said active resin composition comprises the loaded active compound, and said active resin composition comprises less than about 10 μg of the active compound that is unbound to said cation exchange resin for each gram of said active resin composition.

The invention further concerns, inter alia, a process for producing a taste-masked composition comprising a basic active compound and a polymeric matrix having anionic functional groups, said process comprising the steps of loading said polymeric matrix with said active compound to produce a loaded matrix, and washing said loaded matrix with a solvent having a polarity index less than 5.

The invention further concerns, inter alia, a taste masked composition comprising an ion exchange resin and an active compound, wherein said ion exchange resin is weak acid functional groups and said active is dextromethorphan, and wherein said composition is substantially free of unbound dextromethrophan and is adapted to rapidly release said active in the stomach.

DETAILED DESCRIPTION OF THE INVENTION

The invention provides a taste-masked composition containing an active compound that has an ionic moiety. The invention also provides a method for taste-masking active compounds by reversibly adsorbing the active compound in a polymeric matrix or adsorbate. Suitable polymeric matrices have ionic functional groups including anionic groups, e.g., carboxylic, esteric, sulfonic, and phosphonic; and cationic groups, e.g., tertiary amine and quaternary amine. The ionic functional groups of the polymeric matrices reversibly bind the ionic moieties of the active compounds, thereby allowing the active compounds to pass the mouth cavity without significantly releasing the active compounds. One particularly desired embodiment of the invention uses an adsorbate having anionic functional groups to bind basic active compounds having cationic moieties such that the bound active compounds are largely released only when the adsorbate passes the oral cavity and reaches the stomach. The acid in the stomach facilitates the release of the bound active compounds from the adsorbate, thereby making the active compounds available in the gastrointestinal track. For illustration purposes, the present invention is described hereinafter in conjunction with polymeric matrices having anionic functional groups and basic active compounds having cationic moieties.

Various polymeric matrices can be utilized for the invention provided that the polymeric matrices have ionic functional groups that can interact with the ionic moiety of the active compounds and are physiologically compatible, e.g. inert or non-toxic. Exemplary suitable polymeric matrices include weak acidic cation exchange resins having carboxylic acid functional groups, e.g., AMBERLITE® IPR64, IPR88, and PUROLITE® C115E, C115HMR; strong acidic cation exchange resins having a sulfonic acid functional groups, e.g., AMBERLITE® IPR69 and PUROLITE® C100HMR, C100MR; and cation exchange resins having phosphonic functional groups. Particularly desirable polymeric matrices are strong cation exchange resins. Additionally suitable polymeric matrices include copolymers of acrylic and substituted acrylic acids; cellulose esters; vinyl and substituted vinyl esters; and polysulfonic acids, and polysulfonic acid esters, e.g., EUDRAGIT S and PHTHALAVIN. Various ionic forms of such polymeric matrices can be utilized. Particularly desirable are hydrogen, potassium and sodium ionic forms.

Different polymeric matrices having different particle sizes can be utilized, and the particle size of the polymeric matrix can be selected to suit each application. For pharmaceutical application, having a large mean particle size may provide an adverse organoleptic quality, i.e., gritty chewing texture, while having a small mean particle size deteriorates the taste-masking functionalities. As a particularly desirable embodiment of the invention, when a chewable or orally dissolvable delivery application is utilized, it is desirable to have the mean particle size of the polymeric matrix is between about 25 μm (=micrometers) and about 50 μm, more desirably larger than 25 μm but less than 40 μm.

Various active compounds can be taste-masked in accordance with the present invention. One group of suitable active compounds includes pharmaceutical compounds having an amine moiety that is capable of interacting with the anionic functional group of the polymeric matrix. Exemplary suitable pharmaceutical compounds include antitusives, e.g., dextromethorphan; decongestants, e.g., pseudoephedrine; antihistamines, e.g., brompheniramine, chlorpheniramine, diphenhydramine, doxylamine, dexbrompheniramine and loratadine; antidiarrheals, e.g., loperamide; nicotine; and pharmaceutically acceptable salts thereof, e.g., hydrochloride, hydrobromide, maleate, citrate and succinate salts.

To load an active on a polymeric matrix, an active compound is dissolved in a solvent, and the polymeric matrix is contacted with the solution. When a salt form of an active compound is used, it can be dissolved in water; an alcohol, e.g., methanol, ethanol or a mixture thereof; an aqueous solvent; and a mixture thereof. When a free base form of an active compound is used, it can be dissolved in an alcohol. For example, dextromethorphan hydrobromide and diphenhydramine hydrochloride can be dissolved in water or a mixture of water and alcohol. Dextromethorphan or diphenhydramine free base can be dissolved in an alcohol, e.g., ethanol, methanol or a mixture thereof. Once an active solution is prepared, the solution is contacted with a suitable polymeric matrix to allow the active compound to complex or bound to the functional groups of the polymeric matrix. The contacting step of the active compound solution to the polymeric matrix can be repeated with a fresh active compound solution to ensure a high loading of the active compound.

Once the polymeric matrix is loaded with an active compound, the loaded matrix is isolated and washed with a solvent that has a polarity less than an aqueous solvent, preferably with a nonpolar solvent, to remove unbound active compounds. For illustration purposes, the term nonpolar solvent is used hereinafter to indicate nonpolar solvents and solvents having a low polarity. Unlike other known processes that use polar solvents, e.g., water or ethanol, to complete the washing steps of the active-loaded matrix, the use of a nonpolar solvent does not promote dissociation of bound actives from the matrix during the washing step. When a polar solvent is used to wash the loaded matrix, the solvent not only removes unbound active molecules but also causes dissociation of some of the bound active molecule, thereby producing additional unbound active molecules and lowering the concentration of the bound active molecules. The newly created unbound active molecules have a deleterious effect on the effectiveness of taste-masking. However, the loaded matrix can be washed with a polar solvent, such as the solvent that was used to dissolve the active compound, when more than one washing steps are utilized, provided that the last washing step is conducted with a nonpolar solvent. An additional criterion in selecting a solvent is the vapor pressure of the solvent. It is desirable to select a solvent that has a vapor pressure lower than that of an aqueous solvent such that the washed adsorbate can be dried at a lower temperature and with a shorter drying time. Lowering the drying temperature and/or reducing the drying duration are highly advantageous since the lower vapor pressure reduces the cost of drying and prevents temperature-induced degradation of the active compound. Desirably, a nonpolar solvent suitable for the present invention has a polarity index less than 5, preferably less than 4, more preferably less than 3, and most preferably less than 1. A most desired nonpolar solvent has a polarity index of zero. According the present invention, any nonpolar solvents that are known for pharmaceutical applications can be used. Exemplary suitable nonpolar solvents are pentane, hexane, heptane, octane, iso-octane, cyclopentane, cyclohexane, methyl cyclohexane, ethyl cyclohexane, carbon disulfide, trichloroethylene, carbon tetrachloride, benzene, toluene, xylene, propenol, butanol, butanone, and mixtures thereof. Additionally suitable are supercritical fluid and carbon dioxide. Particularly suitable is n-hexane. The washed polymeric matrix is typically air-dried in trays at room or elevated temperature.

The preparation process of the present invention provides a taste-masked active-containing composition with a high active content and is substantially free of unbound active compounds since the process removes unbound active compounds without causing dissociation of bound active compounds. Desirably, at least about 60% of the functional groups of the polymeric matrix are bound by the active compounds, more desirably at least about 70%. Additionally, the loaded, washed polymeric matrix has a high content of the bound active compounds. Desirably, at least about 50 weight % of the loaded polymer matrix is the weight of the loaded active compounds, more desirably at least about 60 weight %.

One desirable embodiment is a highly loaded active-containing composition that utilizes a free base active compound, e.g., diphenhydramine, in conjunction with a strong cation exchange resin, e.g., a sulfonated ion exchange resin. When a free base compound is used, an alcoholic solution, e.g., methanol, ethanol or a mixture thereof, of the active compound is prepared and loaded on the ion exchange resin. The loaded resin can be briefly washed with a relatively small amount of an alcohol before it is washed with a nonpolar solvent, e.g., hexane. Although it is not wished to be bound by any theory, it is believed that using a free base active compound, and not using water or an aqueous solvent, makes high loading of the active compound on the polymeric matrix more practicable. However, it has been found that if the hydrogen ion form of an ion exchange resin is used, the resin itself may provide undesirable organoleptic properties. When the hydrogen form of an ion exchange resin is used, the active-loaded ion exchange resin can be further reacted with a metal ion, e.g., sodium or potassium, to neutralize free or uncomplexed functional groups on the loaded ion exchange resin, thereby further improving the organoleptic characteristics of the loaded resin. Another desirable embodiment of the present invention is a weak cation exchange resin, i.e., an ion exchange resin having carboxylic acid functional groups, e.g., Amberlite IRP 64 or PUROLITE C115HMR, loaded with dextromethorphan free base. It has been found that the loaded matrices of the desirable embodiments efficiently taste mask the active compounds in the mouth and yet readily release the active compounds when the matrices reach the stomach.

In accordance with the present invention, the concentration of an unbound active compound on a loaded resin is determined by suspending a unit amount of the loaded resin in a unit amount of 100% n-hexane for 30 minutes, decanting the hexane and analyzing the decant hexane solution in an HPCL for the presence of the active compound in accordance with the standard USP (United States Pharmcopeia) methods. It is desired that the loaded, washed polymeric matrix is substantially free of unbound active compounds. It is further desired that the loaded, washed polymeric matrix has less than 10 μg (=micrograms) of free active compound per gram of the matrix when the matrix is extracted in n-hexane, more desirably less than 1 μg.

The taste-masked composition can be used in various compositions for oral administrations, including chewable or orally dissolvable forms of pharmaceutical compositions, buccal compositions, syrups and liquid compositions.

The invention is further illustrated with the following examples. It is to be understood that the invention is not limited to the specific embodiments.

EXAMPLE 1

In a 500 ml bottle, 50 g of Amberlite® IRP-69 sulfonic ion exchange resin (Na ionic form) and 150 g of diphenhydramine hydrochloride are placed and deionized water is added to bring the volume to 400 ml. The bottle is shaken for 18 hours and additional 100 g of diphenhydramine hydrochloride is added. The bottle is again shaken for 18 hours. 5 g of the loaded resin is collected and washed twice with 40 ml of deionized water for 5 minutes. The resin is again washed with 40 ml 100% ethanol for 10 minutes, and finally washed with 40 ml of n-hexane (OPTIM grade) for 3 minutes. The washed resin is dried under vacuum at room temperature for 3 hours. The dried loaded resin has 53 wt % of diphenhydramine hydrochloride based on the total weight of the resin, and it does not have any undesirable taste.

EXAMPLE 2

In a 500 ml bottle, 50 g of Purolite® C100HMR sulfonic ion exchange resin (hydrogen ionic form) and 150 g of diphenhydramine free base are placed and 100% ethanol is added to bring the volume to 400 ml. The bottle is shaken for 18 hours and additional 100 g of diphenhydramine is added. The bottle is again shaken for 18 hours. 5 g of the loaded resin is collected and washed twice with 40 ml of ethanol for 5 minutes, twice, and finally washed with 40 ml of n-hexane (OPTIM grade) for 10 minutes. The loaded, washed resin is dried under vacuum at room temperature. In a 500 ml glass beaker, 0.25 g of sodium chloride, 5 g of the dried resinate and 50 ml of water are added and stirred for about 30 minutes. The mixture is filtered through Whatman filter paper #40, and the filtrate is washed with 100 ml of water for three times. The washed resinate is transferred to a 500 ml glass beaker and 50 ml of 100% ethanol is added. The mixture is stirred for 30 minutes and filtered. The alcohol washed resinate is transferred to a 500 ml beaker and washed twice with 50 ml of n-hexane for 10 minutes. The washed resin is dried under vacuum at room temperature for 3 hours. The dried loaded resin has about 50 wt % of diphenhydramine hydrochloride based on the total weight of the resin, and it does not have any undesirable taste.

EXAMPLE 3

1400 g of dextromethorphan free base is dissolved in 12000 ml of USP ethanol. 400 g of PUROLITE C115HMR is placed in a glass bottle and 2000 ml of the dextromethorphan solution is added. The bottle is shaken for 3 hours and the supernatant is drained. 1000 ml of the dextromethorphan solution is added to the bottle and the bottle shaken for another 3 hours. The mixture is transferred into eleven 8 ounce bottles and centrifuged at 200 rpm for 15 minutes at 20° C. The supernatant is drained from the bottle and 100 ml of USP ethanol is added to each bottle and shaken for 5 minutes to wash the loaded resin. The bottles are centrifuged at 200 rpm for 15 minutes at 20° C. The washing step is repeated for additional eight times. The collected loaded resin is placed in a large desiccator and dried by using a freezer dryer at −80° C. and <200 mτ for over night with water bath at less than 45° C. The resulting loaded resin is efficiently taste masked.

EXAMPLE 4

Dissolve 67 g of pseudoephedrine (PSE) free base with 1000 mL of USP ethanol in a 2000 ml glass bottle, mix well (67 mg/ml). Label as PSE stock solution. Pipet 10.0 ml the PSE stock solution into a 100 ml volumetric flask, dilute to volume with USP ethanol. Label as PSE stock. Pipet 10 ml of PSE stock solution into a 100 ml volumetric flask, dilute to volume with USP ethanol. Label this solution as $1^{st}$ dilution (6.7 mg/ml). Pipet 10 ml of the PSE $1^{st}$ dilution solution into a 100 ml volumetric flask, dilute to volume with USP ethanol. Label this solution as 2nd dilution (0.67 mg/ml). Pipet 10 ml of the PSE 2nd dilution solution into a 100 ml volumetric flask, dilute to volume with USP ethanol. Label this solution as 3rd dilution (0.067 mg/ml). Weigh 150 gram of PUROLITE C 100 H MR resin, and transfer it into the 2000 ml glass bottle containing the PSE stock solution. The mixture is shaken for 4 hours. Additional 5.32 gram of resin is added into the PSE/resin complex glass. Decant the solution of PSE/resin complex into a container. Wash the PSE/resin complex with 1000 ml USP ethanol by shaking for 30 minutes. Sonicate the bottle for about one minute and allow the PSE/resin complex to deposit on the bottom of the bottle for about 30 minutes. Decant the top solution and repeat the wash procedure for additional three times. The PSE loaded resin is centrifuged and dried to produce a taste-masked PSE-loaded resin complex.

What is claimed is:

1. A process for producing a taste-masked composition comprising an ionic active compound and a functionalized polymer matrix, said process comprising the steps of loading said functionalized polymer matrix with said active compound to produce a loaded matrix, and washing said loaded matrix with a nonpolar solvent.

2. The process of claim 1, wherein the ionic active compound is a basic active compound and the functionalized polymer matrix is a polymeric matrix having anionic functional groups.

3. The process of claim 1, wherein the nonpolar solvent used for washing the loaded matrix is a solvent having a polarity index less than 5.

4. The process of claim 3 wherein said solvent has a polarity index less than 3.

5. The process of claim 3 wherein said solvent has a polarity index less than 1.

6. The process according to claim 1, wherein said nonpolar solvent is selected from the group consisting of pentane, hexane, heptane, octane, cyclopentane, cyclohexane, methyl cyclohexane, ethyl cyclohexane, and carbon disulfide.

7. The process according to claim 2, wherein the polymeric matrix having anionic functional groups used is a hydrogen form cation exchange resin, and wherein the active-loaded hydrogen form cation exchange resin obtained is further neutralized with a metal ion.

8. The process of claim 7 wherein said metal ion is sodium or potassium.

* * * * *